(12) United States Patent
Jennings

(10) Patent No.: US 7,205,779 B2
(45) Date of Patent: Apr. 17, 2007

(54) APPARATUS AND METHOD FOR MONITORING AND DETERMINING THE MOISTURE CONTENT IN ELASTOMER MATERIALS

(76) Inventor: Thomas A. Jennings, 112A Bala Ave., Bala Cynwyd, PA (US) 19004

( * ) Notice: Subject to any disclaimer, the term of this patent is extended or adjusted under 35 U.S.C. 154(b) by 0 days.

(21) Appl. No.: 10/905,875

(22) Filed: Jan. 25, 2005

(65) Prior Publication Data

US 2006/0164106 A1 Jul. 27, 2006

(51) Int. Cl.
*G01R 27/26* (2006.01)
(52) U.S. Cl. ...................... 324/664; 324/689
(58) Field of Classification Search ........... 324/664, 324/665, 689
See application file for complete search history.

(56) References Cited

U.S. PATENT DOCUMENTS

| | | | |
|---|---|---|---|
| 3,870,951 A | 3/1975 | Brown et al. | |
| 4,352,059 A * | 9/1982 | Suh et al. | 324/664 |
| 4,831,325 A * | 5/1989 | Watson, Jr. | 324/665 |
| 4,909,070 A | 3/1990 | Smith | |
| 5,296,819 A * | 3/1994 | Kuroiwa et al. | 324/664 |
| 6,462,562 B1 * | 10/2002 | Svoboda et al. | 324/664 |
| 6,483,324 B1 * | 11/2002 | Mitter et al. | 324/689 |
| 6,756,793 B2 | 6/2004 | Hirono et al. | |
| 6,784,671 B2 | 8/2004 | Steele et al. | |
| 6,949,937 B2 * | 9/2005 | Knoedgen | 324/658 |

\* cited by examiner

*Primary Examiner*—Andrew H. Hirshfeld
*Assistant Examiner*—Timothy J. Dole
(74) *Attorney, Agent, or Firm*—Malin, Haley & DiMaggio, P.A.

(57) ABSTRACT

An apparatus and method for determining and monitoring the moisture content of an elastomer material used as a closure or stopper for containers holding lyophilized pharmaceutical products, comprising a parallel capacitance circuit formed by supplying a source of AC voltage to a reference elastomer closure and a sample elastomer closure. The capacitance of the sample elastomer closure is measured and compared with the capacitance of the reference elastomer closure. The difference in capacitances of the sample elastomer closure and the reference elastomer closure allow the absorbed moisture content of the sample closure to be determined or monitored. The method does not require destruction of the sample elastomer closure, and can be used to rapidly determine moisture content under normal storage conditions or at elevated or lower temperatures.

15 Claims, 2 Drawing Sheets

APPARATUS AND METHOD FOR MONITORING AND DETERMINING THE MOISTURE CONTENT IN ELASTOMER MATERIALS

FIELD OF THE INVENTION

This invention relates generally to an apparatus and method for monitoring and determining the moisture content of an elastomer material used to seal a container and, specifically, to an apparatus or method for non-destructive monitoring and determining the moisture content of a sample elastomer material.

DESCRIPTION OF RELATED ART

The amount of moisture in a substance is one of the most important factors in determining the useful life of a material. A wide variety of materials used as foods or healthcare products are dried to extend the length of time for which they can be stored. While in most cases excessive moisture shortens the storage time, or shelf life, of a product, there are some substances containing proteins for which the stability, and therefore, the storage time, is actually reduced by over-drying or the removal of too much water. Thus, when producing such substances, the moisture content inside the container must be controlled within certain defined limits to achieve the desired stability and storage time.

One source of moisture that may infiltrate a storage container is found in the elastomer closures and stoppers used to seal containers holding pharmaceutical products. To control the humidity and temperature of a container, care must be taken to ensure that the elastomer closure used to seal the container contains levels of moisture that are within acceptable predetermined limits. The elastomer materials from which the seals on pharmaceutical containers are constructed absorb moisture during steam sterilization. After steam sterilization, an ineffective drying process for the elastomer closures can affect the storage life of the substance held within the container. This absorbed moisture can enter the container during storage resulting in reduced shelf-life and/or contamination of the pharmaceutical product. Once an acceptable moisture content has been attained inside a container, this value must be maintained during storage without being affected by unwanted moisture contamination. Therefore, a means of measuring the moisture content of the elastomer closures used to seal containers is imperative to ensuring that absorbed moisture from the closures does not affect the quality of the substance contained therein.

Current methods for determining the moisture content of an elastomer closure or stopper include measuring the loss in weight of the elastomer material after a repeated drying process is completed, as well as the Karl Fischer method. For the loss in weight method, elastomer closures are first weighed, and then are heated either at atmospheric pressure or in a vacuum in the presence of a desiccant. The elastomer closures are then weighed again and the drying process is repeated until the weight of the elastomer closures reaches a predetermined acceptable limit. The loss in weight of the elastomer closures represents the moisture content that has been removed during the drying process by heating and evaporation. Several disadvantages are inherent in the loss of weight method for determining the moisture content of elastomer materials. First, the method assumes that all of the moisture was removed from all of the elastomer closures undergoing the drying process. However, some of the elastomer closures in a batch that has undergone the drying process may still contain, for various reasons, substantial quantities of moisture. Therefore, when using the loss in weight method, there is no current means for establishing that all of the elastomer closures in a batch have been dried to an acceptable final predetermined value.

The second disadvantage in using the loss in weight method to determine the moisture content of elastomer closures is that the loss in weight measured after completion of the drying process represents an average moisture content value for the entire batch of elastomer closures for which the moisture content is being determined. If the elastomer closures selected to be weighed are primarily those nearest the porous medium through which the moisture escapes during drying, then the moisture content determined for the batch will be low. However, if the elastomer closures selected to be weighed are mainly those that were located nearest the plastic cover during drying, then the determined moisture content for the batch would represent a much higher value. Moreover, there is no method for determining the frequency distribution in a batch of elastomer closures that were near the porous material as opposed to those that were near the plastic cover during the drying process.

Additional disadvantages to using the loss in weight method for determination of moisture content include the problem that the moisture content determined for one bag of elastomer closures may not be equal to the moisture content of another bag of elastomer closures that simultaneously underwent the drying process. The loss in weight method also does not provide a means for establishing a base moisture content value at which an elastomer closure is considered to be dry, nor does the method provide a means for identifying those elastomer closures that contain unacceptable amounts of moisture.

The Karl Fischer method has been used to determine the moisture content of a single elastomer closure. In this method, the elastomer closure is cut into a number of sections that are placed in methanol or some other suitable Karl Fischer agent to remove moisture from the closure. The presence of water in the methanol or other reagent is then titrated with a Karl Fischer solution that reacts with water to form colorless hydrogen iodide. When there is no more water available in the solution to form hydrogen iodide, free iodine, which has color, appears, thereby indicating an end point before which the conductivity of the solution will change. By measuring the amount of hydrogen iodide formed, the amount of moisture in the elastomer closure can be determined.

One disadvantage to using the Karl Fischer method for determining the moisture content of an elastomer closure is that the methanol or Karl Fischer reagent may not completely remove all of the moisture from the closure causing the results of the method to be unreliable in industries such as pharmaceuticals where accuracy and precision are required. In addition, this method requires that the elastomer closure be cut into sections which raises the possibility that the sectioning of the closure could increase or decrease the moisture content of that closure. The method also requires the destruction (by cutting into sections) of the elastomer closure for which the moisture content is being determined. Thus, the Karl Fischer method is not useful for monitoring the moisture content of individual elastomer closures. Finally, the Karl Fischer method is time-consuming and inefficient, and therefore, is not useful for analyzing sufficient numbers of elastomer closures to obtain a frequency distribution of the moisture in a batch of closures.

U.S. Pat. No. 6,784,671, issued to Steele et al., on Aug. 31, 2004, describes a moisture and density detector for estimating moisture content of dielectric materials by passing a radio frequency signal through the dielectric material between opposed or adjacent electrodes. The '671 patent differs from the applicant's invention in that it requires a source of radio frequency signal rather than utilizing a source of AC voltage to determine capacitance. The '671 patent also requires a micro-processor for measuring and comparing the signal strength and phase shift of the radio frequency signal as it passes through a dielectric material, such as rubber. The inclusion of the radio signal generating device and the microprocessor increases the manufacturing and maintenance costs as well as the complexity of the invention, thereby making the '671 invention less desirable for use in measuring moisture content in elastomer materials. Moreover, the '671 patent does not include a parallel capacitance circuit that can be used to detect differences in capacitance between reference and sample rubber pieces.

U.S. Pat. No. 3,870,951, issued to Brown et al., on Mar. 11, 1975, describes a moisture measuring probe for insertion into bulk materials where moisture content is to be measured. However, unlike the applicant's invention, the '951 patent requires that the probe be placed in direct contact with the subject material by inserting said probe into the bulk material for which moisture content is to be measured.

U.S. Pat. No. 4,909,070, issued to Smith on Mar. 20, 1990, describes a moisture sensor for detecting moisture content in particulate materials, and particularly in soil, by measuring changes in the capacitance of the capacitance-sensing probe. This invention also requires that the sensor be inserted into the soil or other material for direct contact between the sensor and the particulate matter for which the moisture content is to be determined.

U.S. Pat. No. 6,756,793, issued to Hirono et al., on Jun. 29, 2004, describes a capacitance-type moisture sensor that determines the moisture content of garbage or other material that passes through the electric field generated between two electrodes. This invention includes a sensor housing that has an electrically-insulating wall with a pair of electrodes disposed on its surface and a circuit unit including a capacitance-detecting circuit. The electrodes are positioned on the inner surface of the electrically-insulating wall while the outer surface of said wall faces a space in which the moisture content is to be measured. The electric field produced at radio frequencies between the two electrodes forms the moisture-detecting region of the capacitance-detecting circuit. The '793 patent teaches that the oscillating circuit oscillates within a range of several ten to several hundred MHz, which frequencies fall within the radio frequency band. An output circuit produces an electrical signal that corresponds to the amounts of water based upon the capacitance value determined by the capacitance-detecting circuit. The '793 invention is particularly well-adapted for measuring the moisture content of garbage contained in a garbage vessel. This invention requires the use of radio frequencies and placement inside the container holding the material for which the moisture content is to be measured, and thus, is not effective for determining the moisture content of a solid elastomer closure or stopper.

SUMMARY OF THE INVENTION

An apparatus and method for determining and monitoring the moisture content of an elastomer material used as a closure or stopper for containers holding lyophilized pharmaceutical products, comprising a parallel capacitance circuit formed by supplying a source of AC voltage to both a reference elastomer closure and a sample elastomer closure. Each elastomer closure is placed into a holding assembly that is comprised of a first electrode that also serves as a holder, a second electrode, an insulator plate, insulated supports, and an insulated base. The first and second electrodes of each holding assembly are connected to a capacitance meter that supplies AC voltage to the circuit. The capacitance of the sample elastomer closure is measured and compared with the capacitance of the reference elastomer closure. The difference in capacitances of the sample elastomer closure and the reference elastomer closure allow the absorbed moisture content of the sample closure to be determined or monitored. The method does not require destruction of the sample elastomer closure, and can be used to rapidly determine moisture content under normal storage conditions or at elevated or lower temperatures.

An object of this invention is to create a method and apparatus for the non-destructive monitoring of moisture content in an elastomer enclosure or stopper.

Another object of this invention is to create an apparatus and method for determining the amount of time that elastomer closures can be exposed to a given humidity at a given Temperature before the residual moisture absorbed in the closures reaches an unacceptable value.

Still another object of this invention is to provide an inexpensive and simple apparatus and method for measuring the moisture content of an elastomer material.

In accordance with these and other objects which will become apparent hereinafter, the instant invention will now be described with particular reference to the accompanying drawings.

DETAILED DESCRIPTION

The capacitance of a pair of opposite (positive and negative) electrodes spaced apart is a function of the dielectric material placed in the electric field generated between the electrodes.

Figure 1:
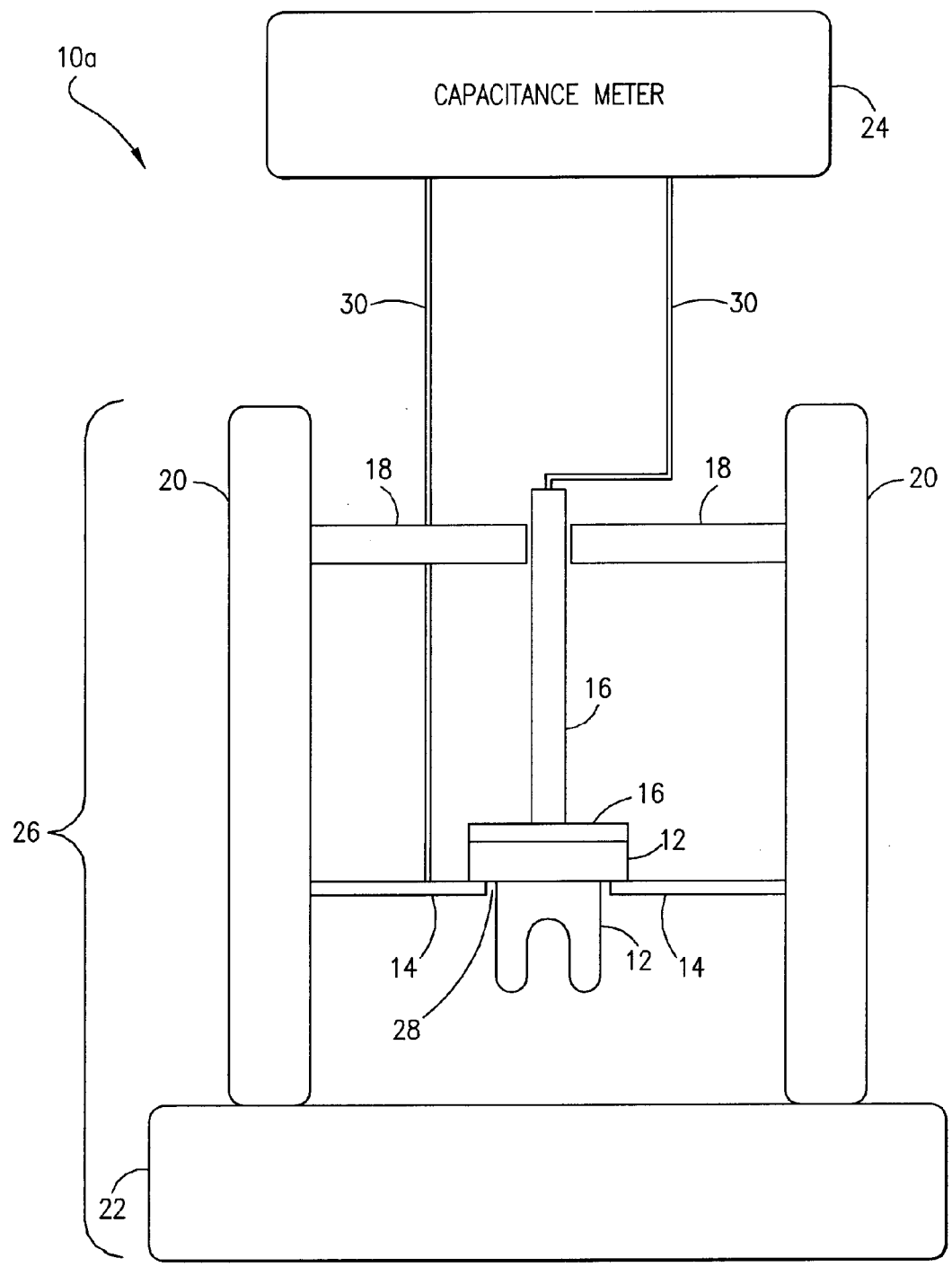
FIG. 1 shows a schematic diagram of the invention as it is used for a direct measurement of the moisture content of an elastomer material.

FIG. 1 illustrates a direct measurement apparatus 10a for directly determining and monitoring the moisture content of an elastomer material 12 used as a closure 12 or stopper 12 for a container holding a lyophilized pharmaceutical product. The apparatus 10a comprises a first electrode 14 for contacting and holding the elastomer material 12, a second electrode 16 that contacts the top surface of the elastomer material, an insulator plate 18 to guide and maintain the second electrode 16 in position, one or more insulated supports 20 to which said insulator plate 18 is attached, a base 22 to support the insulated supports, said base being constructed from an electrical insulator material, and a capacitance meter 24 that provides a known frequency of AC voltage to electrodes 14 and 16 to be supplied to the elastomer material. The first electrode 14 is preferably plate-shaped and includes a central aperture 28 for receiving and holding the elastomer closure 12 which is placed inside said aperture 28 of the first electrode 14. The elastomer closure 12 contacts the sides of the first electrode 14 inside the electrode aperture 28 so that said elastomer closure 12 can receive the AC voltage that is supplied by the capacitance meter 24. The first electrode 14 and second electrode 16 are connected to said elastomer material 12 and said capacitance meter 24 to supply the AC voltage from said capacitance meter 24 to said sample elastomer material 12, each electrode 14 and 16 having a known surface area. The first electrode 14, second electrode 16, insulator plate 18, insulated supports 20, and base 22 together comprise a holding assembly 26 for engaging the elastomer closure or stopper 12 for which the absorbed moisture content is to be determined.

The second electrode 16 is placed in contact with the top surface of the elastomer closure 12 so that said second electrode 16 is oriented perpendicular to the first electrode 14. The first electrode 14 and second electrode 16 may be constructed from any known electrical conductor material, including stainless steel. A plurality of wires 30 connecting said first and second electrodes 14 and 16 to form the capacitance circuit may also be constructed from any known electrical conductors. By measuring the capacitance of the elastomer material 12 between electrodes 14 and 16 and comparing the measured capacitance value with the capacitance of a known dry standard elastomer, the amount of moisture in the sample elastomer material 12 can be calculated.

In the present invention, the capacitance of a reference system using an elastomer closure that contains no moisture or a known amount of moisture is compared with the capacitance of the sample elastomer closure whose moisture content is being measured in that the reference elastomer closure and the sample elastomer closure are the dielectric materials placed in the compared electric fields. The quantitative difference between the capacitances can be used to precisely calculate the moisture content of the sample elastomer closure.

Figure 2:
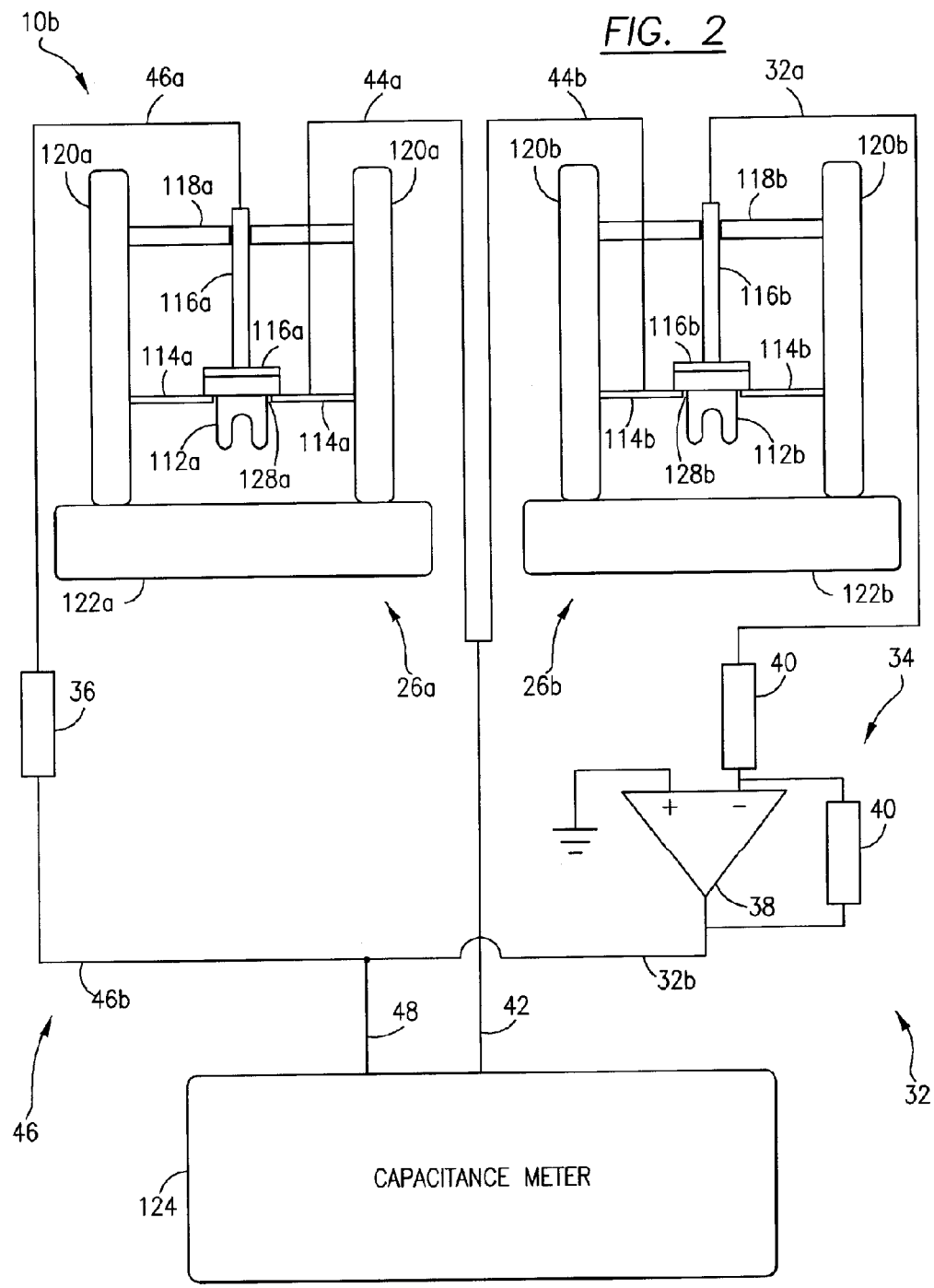
FIG. 2 shows a schematic diagram of the invention and its parallel capacitance circuit.

FIG. 2 illustrates a differential measurement apparatus 10b as the preferred embodiment of the invention. The differential measurement apparatus 10b determines and monitors the moisture content of an elastomer material used as a closure or stopper for a container holding a lyophilized pharmaceutical product. Said apparatus 10b determines the absorbed moisture content of a sample elastomer closure 112a by measuring the difference in capacitance of said sample closure 112a as compared to the capacitance of a reference elastomer closure 112b. Preferably, said reference elastomer closure 112b will contain no absorbed moisture, however, a reference elastomer closure containing a known predetermined quantity of moisture may also be utilized without affecting the accuracy of measurements taken using apparatus 10b.

The differential measurement apparatus 10b comprises a first holding assembly 26a into which a sample elastomer closure 112a is placed and a second holding assembly 26b into which a reference elastomer closure 112b with known dielectric properties is placed. The first holding assembly 26a comprises a first electrode 114a including a central aperture 128a, a second electrode 116a, an insulator plate 118a, one or more insulated supports 120a, and a base 122a for engaging the sample elastomer closure 112a. Similarly, said second holding assembly 26b comprises a first electrode 114b including a central aperture 128b, a second electrode 116b, an insulator plate 118b, one or more insulated supports 120b, and a base 122b for engaging the reference elastomer closure 112b.

The differential measurement apparatus 10b further comprises a capacitance meter 124 that provides a known frequency of AC voltage to both the sample and reference elastomer materials 112a and 112b, output circuits 32 and 46, an inverting circuit 34 connected to said capacitance meter 124 and said output circuit 32, and a source of electrical resistance 36 in said output circuit 46 of said sample elastomer material, whereby electrical differences between the sample elastomer material 112a and the reference elastomer material 112b, such as differences in capacitance, can be used to determine the moisture content of the sample elastomer material.

The inverting circuit 34 of apparatus 10b amplifies the output of the reference elastomer material 112b by a factor of 1 and changes the sign of the reference output signal. The sign inverting circuit 34 comprises an operational amplifier 38 and two resistors 40. The resistance provided by the resistor 36 in the output of said sample elastomer material 112a matches the time constant of the output of the reference elastomer material 112b to ensure that the time constants of the two outputs are equal.

As shown in FIG. 2, output circuit 32 comprises wires 32a and 32b and inverting circuit 34 to conduct the output signal of the reference elastomer material 112b from second electrode 116b to the capacitance meter 124. The output circuit 46 for the sample elastomer material 112a comprises wires 46a and 46b and resistor 36 to conduct the output signal of said sample closure from second electrode 116a to the capacitance meter 124. Both output circuits 32 and 46 connect at wire 48 which passes into capacitance meter 124. Wire 48 forms an output circuit that receives and combines the output signals from output circuit 32 of the reference elastomer material 112b and output circuit 46 of the sample elastomer material 112a.

The differential measurement apparatus 10b includes a sample elastomer material circuit and a reference elastomer material circuit, neither of which are labeled by reference number in the drawings. The sample elastomer material circuit is comprised of the sample elastomer material 112a, electrodes 114a and 116a of said first holding assembly 26a, the capacitance meter 124, the output circuit 46, and the source of resistance 36, all of which are connected together by wires 42, 44a, 46a, 46b and 48, as shown in FIG. 2. The reference elastomer material circuit is comprised of the reference elastomer material 112b, electrodes 114b and 116b of said second holding assembly 26b, the output circuit 32, the inverting circuit 34 connected to said capacitance meter 124 and said output circuit 32, and the sources of electrical resistance 40, all of which are connected together by wires 42, 44b, 32a, 32b and 48, as illustrated in FIG. 2. Wire 48, which receives the output signals from output circuit 46 and output circuit 32, connects to capacitance meter 124 and comprises the difference in capacitance between the sample and reference elastomer material circuits. The connection of said sample elastomer material 112a and the reference elastomer material 112b to a source of AC voltage in capacitance meter 124 forms a parallel capacitance circuit.

Usage of the differential measurement apparatus 10b to determine the absorbed moisture content of a sample elastomer closure 112a by comparison of said sample closure's capacitance with the capacitance of a reference elastomer closure 112b is preferred because said apparatus 10b provides a more accurate measurement than use of the direct measurement apparatus 10a, which does not permit the comparison of sample closure capacitance with the capacitance of a reference closure. An amplifier, which is not shown in the drawings, can be used in the output circuit formed by wire 48 to amplify the output difference in capacitance between the sample elastomer material circuit and the reference elastomer material circuit to enhance the sensitivity of the moisture measurement.

A method for determining and monitoring the absorbed moisture content of a sample elastomer material 112a, including both elastomer closures 112a and elastomer stoppers 112a, includes the steps of: first, creating a reference elastomer closure 112b, and second, measuring and comparing the capacitance of said reference elastomer closure with the capacitance of the sample elastomer closure 112a. To form a reference elastomer closure 112b, the capacitance of which can be compared with the capacitance of a sample elastomer closure 112a, first, the moisture content of the reference closure must be determined. To determine the absorbed moisture content of the intended reference elastomer closure 112b said closure is placed into the central aperture 28 of the first electrode 14 of a holding assembly 26 of a direct measurement apparatus 10a. A capacitance meter 24 supplies AC voltage to said reference closure 112b so that the capacitance of said reference closure can be measured.

Once the capacitance of the reference elastomer closure 112b has been measured, said closure is removed from the first electrode 14 of holding assembly 26 and subsequently, said closure is weighed. The reference elastomer closure 112b is then dried until the capacitance at a given temperature and at relative humidity is equivalent to $C_0 +/- \sigma$ farads, where $\sigma$ is the standard deviation for a frequency distribution of dry elastomer closures. After completion of the drying process, the reference elastomer closure 112b is weighed again, and the change in mass of the closure determined by the second weighing represents the mass of the absorbed moisture that was in the elastomer closure. In another embodiment of the invention, the reference elastomer closure 112b may contain a predetermined, known quantity of absorbed moisture rather than being completely dried until absent of any moisture.

The presence of residual moisture in an elastomer closure used as a dielectric material in an electric field alters the dielectric properties of the closures resulting in variations in capacitance depending upon the amount of moisture absorbed within each closure. For example, at a given temperature, applied voltage, and frequency, the capacitance of an elastomer closure will increase. The capacitance of an elastomer closure in the absence of any absorbed moisture is defined by the following equation:

$$C_0 = \epsilon(A/d) \text{ farads},$$

where $\epsilon$ is the dielectric constant for the elastomer material, A is the area (m$^2$) being tested, and d (meters) is the thickness of the elastomer material. As an elastomer closure absorbs water, the capacitance of the elastomer closure will increase to $C_i$. By establishing a relationship between $C_i$ and the amount of moisture in the closure, one can determine the amount of absorbed moisture in another elastomer closure within defined limits. Thus, the relationship between the amount of moisture in an elastomer closure and the capacitance of the closure used as a dielectric material permits the determination of the amount of absorbed moisture in the closure by measuring the capacitance, or another parameter such as quality factor, dissipation factor, or reactance.

To determine or monitor the absorbed moisture content of a sample elastomer closure 112a, said sample closure is placed into the central aperture 128a of the first electrode 114a of the first holding assembly 26a and the reference closure 112b is placed into aperture 128b of the first electrode 114b of the second holding assembly 26b. The capacitance meter 124 supplies AC voltage to both the sample elastomer closure 112a placed into the first holding assembly 26a and to the reference elastomer closure 112b that is placed within the second holding assembly 26b. The first holding assembly 26a of the sample elastomer circuit and the second holding assembly 26b of the reference elastomer circuit each are connected to resistors 36 and 40, respectively. The sample elastomer circuit and the reference elastomer circuit together form a parallel capacitance circuit from which the absorbed moisture content of the sample elastomer closure 112a can be determined by comparing the dielectric properties, e.g., the capacitance, of said sample and said reference elastomer closures 112a and 112b. Although capacitance is the preferred dielectric property to be measured for determining the moisture content of an elastomer material, other dielectric properties, including reactance, quality factor, and dissipation factor, may also be measured to determine moisture content.

The moisture content of a sample elastomer closure 112a is determined by measuring and comparing the capacitance of the absorbed moisture of both the reference elastomer closure 112b and said sample elastomer closure. For example, the capacitance of the elastomer material is determined by the equation:

$$M_r = C_i - C_r,$$

where $M_r$ represents the residual moisture in the sample elastomer closure, $C_i$ represents the capacitance of the sample elastomer closure, and $C_r$ represents the capacitance of the reference elastomer closure preferably absent any moisture. The difference in capacitance obtained using the equation above is used to determine the presence of water absorbed in the sample elastomer closure.

As described above, the moisture content of a sample elastomer material 112a is measured by determining the electrical properties of said sample elastomer material with respect to the reference elastomer material 112b, which contains no absorbed moisture or a known quantity of absorbed moisture. The amount of residual moisture absorbed in the sample elastomer material 112a is determined by the dielectric properties of the elastomer material, including the capacitance of said elastomer material. This method for monitoring and determining the moisture content of an elastomer material 112a is advantageous over current methods in that the moisture content of said elastomer material is determined without destroying the elastomer closure 112a or stopper 112a being examined. Moreover, the change in moisture content of a given elastomer material 112a can be determined and monitored under normal storage conditions or at elevated or decreased humidity and temperature.

The invention provides a novel and convenient method to accurately and quickly determine the moisture content within a sample elastomer closure 112a to be used as a seal for a container holding a lyophilized pharmaceutical product. The apparatus may also be used to measure the moisture content of elastomer closures and stoppers used with containers holding substances other than lyophilized pharmaceutical products which also require protection from moisture infiltration during storage, such as foods, cosmetics, and electrical devices. The present invention also has the benefit that measurements taken using this method do not require destruction of any of the sample elastomer closures during the measuring process.

Elastomer closures are steam-sterilized in bags. After sterilization, the closures undergo the drying process which has the unwanted result that not all closures will have the same absorbed moisture content. The present invention provides a faster, more efficient, non-destructive method for determining the residual moisture absorbed within each individual closure so that closures containing excessive moisture can be dried further before being used as a protective seal on a container holding a lyophilized pharmaceutical product. Thus, the invention provides a safeguard in the manufacturing process to ensure that moisture does not contaminate the stored product by introduction from the elastomer closure sealing a given container. The method and apparatus can also be used to determine the moisture content of elastomer closures being used on products under storage to ascertain whether excessive moisture is being absorbed by the elastomer material under normal storage conditions. This method could be beneficial to test for either a random failure or a general failure of a particular elastomer closure or stopper.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An apparatus for directly monitoring and determining the moisture content of an elastomer material, comprising:
   a capacitance meter that provides a known frequency of AC voltage; and
   a holding assembly for receiving a sample elastomer material, said holding assembly comprising:
      a holder that acts as a first electrode to apply the AC voltage from said capacitance meter to said sample elastomer material, said holder including a central aperture into which the sample elastomer material is placed;
      a second electrode for contacting the top surface of the sample elastomer material, said second electrode supplying the AC voltage from said capacitance meter simultaneously as the first electrode to said sample elastomer material;
      an insulator plate to guide and maintain said second electrode in position;
      one or more insulated supports to which said insulator plate is attached; and
      a base to support said insulated supports, said base being constructed from an electrical insulator material.

2. The invention according to claim 1, wherein the first electrode and second electrode may be constructed from any known electrical conductor, including stainless steel.

3. The invention according to claim 1, wherein a plurality of wires connect said first electrode and said second electrode to form a capacitance-measuring circuit, said wires being constructed from any known electrical conductor.

4. A method for monitoring the moisture content of a sample elastomer material in which the absorbed moisture in said sample elastomer material is measured by determining the difference between the electrical properties of said sample elastomer material and a reference elastomer material, at an identical given temperature and humidity, and electrically comparing those determined electrical properties of the sample elastomer material with the electrical properties of the reference elastomer material;
   providing an apparatus wherein the apparatus used with said method for directly monitoring the moisture content of the sample elastomer material, comprises the following:
      a capacitance meter that provides a known frequency of AC voltage;
      an insulated holding assembly for receiving said sample elastomer material, said holding assembly including a central aperture into which the sample elastomer material is placed;
      a first electrode for engaging the sample elastomer material to apply the AC voltage from said capacitance meter to said sample elastomer material;
      a second electrode for engaging the sample elastomer material to supply the AC voltage from said capacitance meter simultaneously as the first electrode to said sample elastomer material; and
      the reference elastomer material, said reference elastomer material having known moisture content to which the electrical properties of the sample elastomer material can be compared to monitor the moisture content of said sample elastomer material; and
         wherein the reference elastomer material contains no absorbed moisture or a known quantity of absorbed moisture.

5. The method according to claim 4, wherein the amount of residual moisture absorbed in the elastomer material is monitored by monitoring the dielectric properties of the elastomer material, including the capacitance, reactance, dissipation factor, or quality factor, but preferably by the capacitance.

6. The method according to claim 4, wherein the moisture content of elastomer materials is monitored without destroying any items manufactured from the elastomer material.

7. The method according to claim 4, wherein the change in moisture content of a given elastomer material can be monitored under normal storage conditions or at elevated or decreased humidity and temperature.

8. The method according to claim 4, wherein capacitance is me preferred dielectric property of the sample and reference elastomer materials that is to be monitored.

9. An apparatus for directly monitoring and determining the moisture content of an elastomer material, comprising:
   a capacitance meter that provides a known frequency of AC voltage;
   an insulated holding assembly for receiving a sample elastomer material, said holding assembly including a central aperture into which the sample elastomer material is placed;
   a first electrode for engaging me sample elastomer material to apply the AC voltage from said capacitance meter to said sample elastomer material;
   a second electrode for engaging the sample elastomer material to supply the AC voltage from said capacitance meter simultaneously as the first electrode to said sample elastomer material; and
   a reference elastomer material, said reference elastomer material having known moisture content to which the measured electrical properties of the sample elastomer material can be compared to determine and to monitor the moisture content of said sample elastomer material.

10. An apparatus for directly monitoring and determining the moisture content of an elastomer material, comprising:
   means for holding a sample elastomer material, said means for holding including a central aperture into which the sample elastomer material is placed;
   means for electrically contacting said sample elastomer material;
   means for supplying a known frequency of AC voltage to said sample elastomer material;
   means for measuring the capacitance of said sample elastomer material; and
   a reference elastomer material, said reference elastomer material having known moisture content to which the measured electrical properties of the sample elastomer material can be compared to determine and to monitor the moisture content of said sample elastomer material.

11. A method for determining the moisture content of a sample elastomer material by determining the difference between the electrical properties of said sample elastomer material and a reference elastomer material, at an identical given temperature and humidity, and electrically comparing those determined electrical properties of the sample elastomer material with the electrical properties of the reference elastomer material;

providing an apparatus wherein the apparatus used with said method for directly determining the moisture content of the sample elastomer material, comprises the following:

a capacitance meter that provides a known frequency of AC voltage;

an insulated holding assembly for receiving said sample elastomer material, said holding assembly including a central aperture into which the sample elastomer material is placed;

a first electrode for engaging the sample elastomer material to apply the AC voltage from said capacitance meter to said sample elastomer material;

a second electrode for engaging the sample elastomer material to supply the AC voltage from said capacitance meter simultaneously as the first electrode to said sample elastomer material; and the reference elastomer material, said reference elastomer material having known moisture content to which the electrical properties of the sample elastomer material can be compared to determine the moisture content of said sample elastomer material; and wherein the reference elastomer material contains no absorbed moisture or a known quantity of absorbed moisture.

12. The method according to claim 11, wherein the amount of residual moisture absorbed in the elastomer material is determined from the dielectric properties of the elastomer material, including the capacitance, reactance, dissipation factor, or quality factor, but preferably by the capacitance.

13. The method according to claim 11, wherein the moisture content of elastomer materials is determined without destroying any items manufactured from the elastomer material.

14. The method according to claim 11, wherein the change in moisture content of a given elastomer material can be determined under normal storage conditions or at elevated or decreased humidity and temperature.

15. The method according to claim 11, wherein capacitance is the preferred dielectric property of the sample and reference elastomer materials that is to be measured.

* * * * *